US008235974B2

(12) United States Patent
Wagnieres et al.

(10) Patent No.: US 8,235,974 B2
(45) Date of Patent: Aug. 7, 2012

(54) METHOD FOR HAIR REMOVAL

(75) Inventors: Georges Wagnieres, Lutry (CH);
Norbert Lange, Nyon (CH); Nora Dögnitz, Lausanne (CH); Denis Salomon, Petit-Lancy (CH); Hubert Van Den Bergh, St-Sulpice (CH)

(73) Assignee: Ecole Polytechnique Federale de Lausanne (EPFL), Lausanne (CH)

( * ) Notice: Subject to any disclaimer, the term of this patent is extended or adjusted under 35 U.S.C. 154(b) by 2058 days.

(21) Appl. No.: 10/495,803

(22) PCT Filed: Nov. 15, 2002

(86) PCT No.: PCT/CH02/00616
§ 371 (c)(1),
(2), (4) Date: Jan. 6, 2005

(87) PCT Pub. No.: WO03/041673
PCT Pub. Date: May 22, 2003

(65) Prior Publication Data
US 2005/0124984 A1 Jun. 9, 2005

(30) Foreign Application Priority Data
Nov. 16, 2001 (EP) .................................... 01811103

(51) Int. Cl.
*A61B 18/20* (2006.01)

(52) U.S. Cl. ........................................... 606/9; 128/898

(58) Field of Classification Search ................ 606/2–19, 606/133; 607/88–94; 128/898; 424/59–60, 424/94.1, 9.6, 70.1
See application file for complete search history.

(56) References Cited

U.S. PATENT DOCUMENTS

| 5,520,905 A * | 5/1996 | Uhlmann et al. ............... 424/59 |
| 5,669,916 A | 9/1997 | Anderson |
| 5,998,597 A * | 12/1999 | Fisher et al. ................. 536/23.1 |
| 2002/0087205 A1 * | 7/2002 | Chen .............................. 607/88 |
| 2003/0028227 A1 * | 2/2003 | Neuberger et al. ............. 607/88 |
| 2005/0075703 A1 * | 4/2005 | Larsen ............................ 607/88 |

FOREIGN PATENT DOCUMENTS

| GB | 2326335 A | 12/1998 |
| WO | WO 96 28412 A | 9/1996 |
| WO | WO 0071089 A | 11/2000 |

OTHER PUBLICATIONS

Fingar et al., Photodynamic Theraoy Using a Protoporphyrinogen Oxidase Inhibitor, Oct. 17, 1997, Cancer Research, vol. 57, 4551-4556.*

(Continued)

*Primary Examiner* — Henry M Johnson, III
*Assistant Examiner* — Jeffrey Lipitz
(74) *Attorney, Agent, or Firm* — Charles E. Lyon; Kristen C. Buteau; Choate, Hall & Stewart LLP

(57) ABSTRACT

A method for hair removal from a skin area by selective photo-inactivation of the pilo-sebaceous apparatus using derivatives of ALA with alkylene-glycol chains. Selectivity of the method is further enhanced by treatment of the epidermis by agents reducing PpIX levels in the epidermis. Side effects are diminished by using short drug/light intervals.

18 Claims, 5 Drawing Sheets

OTHER PUBLICATIONS

Hirschberg et al., ALA- and ALA-ester mediated photodynamic therapy of human glioma spheroids, Mar. 2002, Jornal or Neuro-Oncology, 57, 1-7.*

Berger et al., Ethylene Glycol and Amino Acid Derivatives of 5-Aminolevulinic Acid as New Photosensitizing Precursors of Protoporphyrin IX in Cells, Journal of Medicinal Chemistry, American Chemical Society, U.S. vol. 43, No. 25, Dec. 2000, pp. 4738-4746.

Lang, et al., "The 5-aminolevulinic acid-induced porphyrin biosynthesis in benign and malignant cells of the skin," *Journal of Photochemistry and Photobiology B: Biology*, vol. 65: 29-34 (2001).

Stryer, "Porphyrine werden in Säugern aus Glycin and Succinyl-Coenzym A synthetisiert," *Biochemie*, $3^{rd}$ edition: 620-621 (1988).

Dietel, et al., "Formation of water-soluble porphyrins and protoporphyrin IX in 5-aminolevulinicacid-incubated carcinoma cells," *Journal of Photochemistry and Photobiology B: Biology*, vol. 33: 225-231 (1996).

Menon, et al., "A Comparison of the Phototoxicity of Protoporphyrin, Coproporphyrin and Uroporphyrin Using a Cellular System in Vitro," *Clinical Biochemistry*, vol. 22: 197-200 (1989).

\* cited by examiner

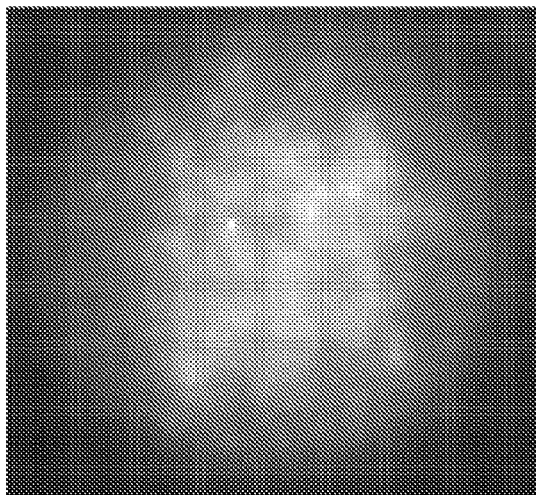
Figure 1A: Ratio 1.46
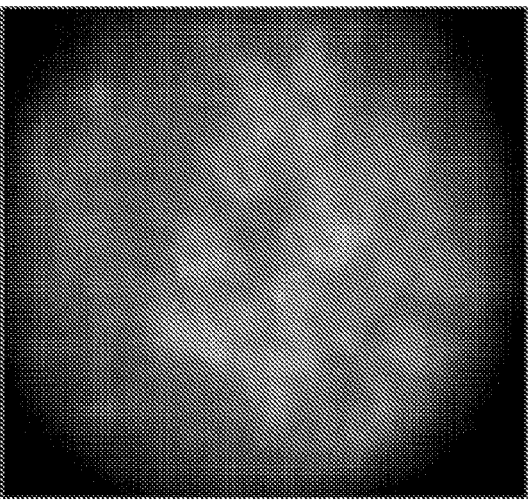
Figure 1B: Ratio 2.53
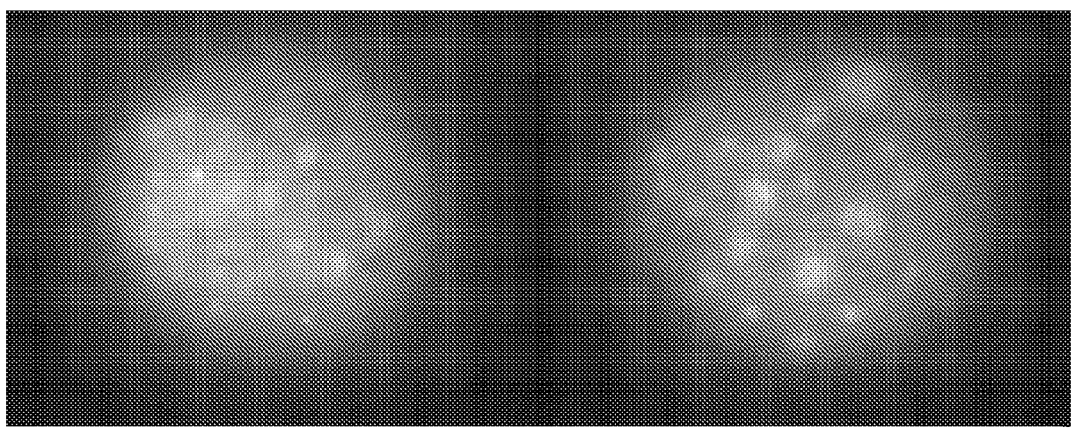
Figure 2A: Ratio 1.93
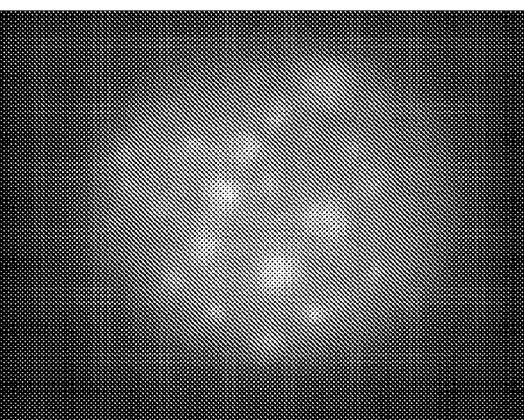
Figure 2B: Ratio 5.95
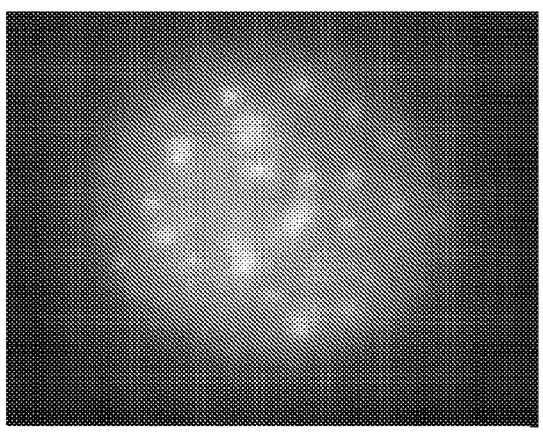
Figure 2C: Ratio 7.15

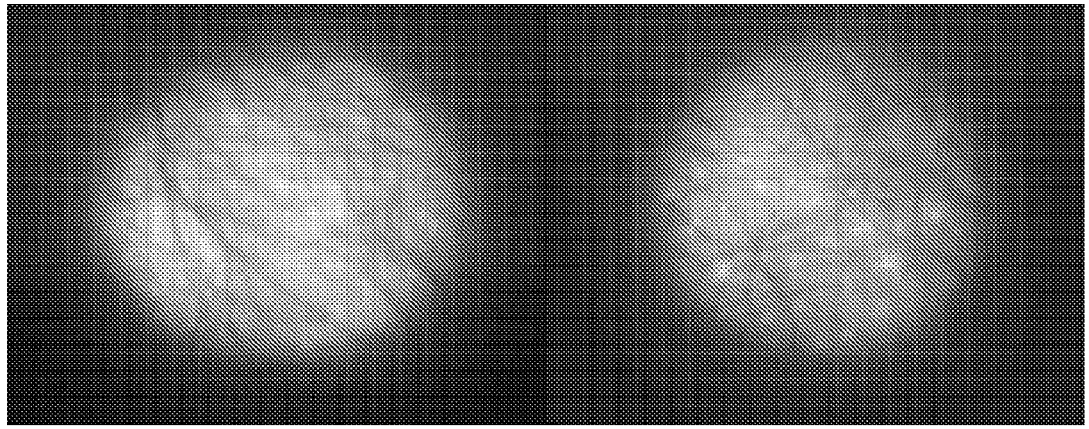
Figure 3A: Ratio 1.62    Figure 3B: Ratio 2.51
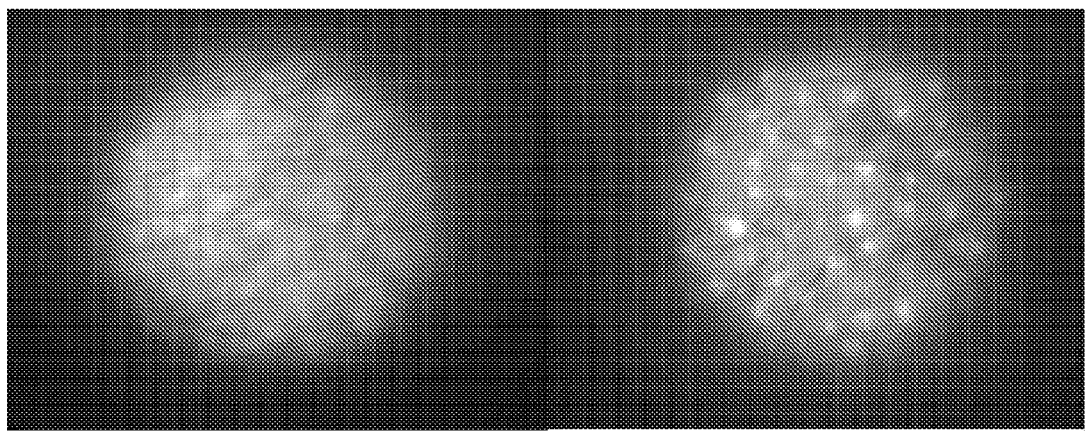
Figure 4A: Ratio 2.21    Figure 4B: Ratio 3.24
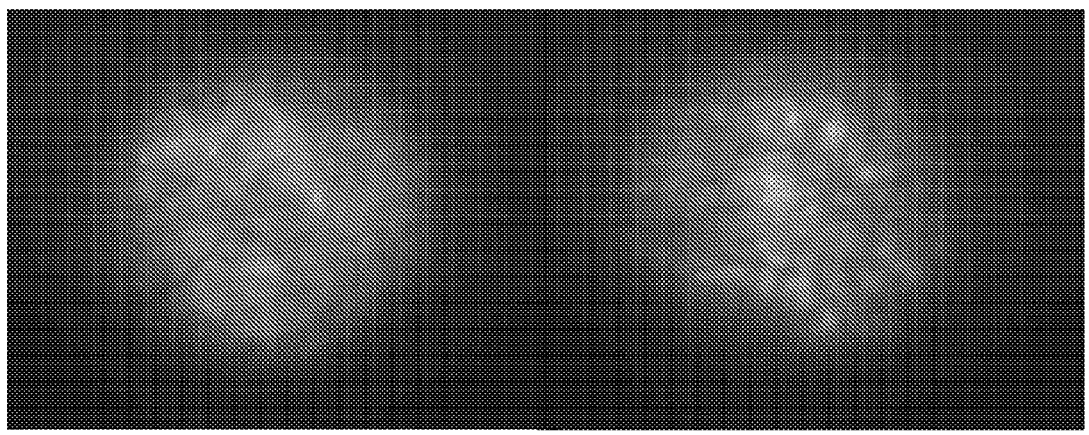
Figure 5A: Ratio 3.47    Figure 5B: Ratio 4.72

METHOD FOR HAIR REMOVAL

Currently, the most common methods for hair removal involve the use of hair removal creams, as well as shaving, waxing and electrolysis. Although creams and shaving are popular because they can be readily used at home, they are inadequate because they must be used on a very regular basis. Electrolysis offers longer-term hair removal. This method, however, can be time-consuming, is often quite painful and expensive.

Lasers, lamps and other sources of electromagnetic radiation are being increasingly utilized for the removal of unwanted hair, and for at least inhibiting, and in some instance preventing, the regrowth thereof. Examples of such epilation techniques are disclosed by U.S. Pat. No. 5,227,907 and U.S. Pat. No. 5,425,728 (to Tankovich), describing topical formulations containing a substance having high absorption at a frequency band of light, and capable to infiltrate a hair duct. Such substances may be carbon particles, hematoporphyrin and/or various dyes. The formulation is applied to the skin, the excess is removed and the skin is illuminated with an appropriate light source so that the energy absorbed is sufficient to cause reactions, which destroy hairs or ducts or follicles, or tissues surrounding said follicles. Such treatments are generally not satisfactorily selective, in that they damage surrounding tissues instead of the hair follicle itself, and may provoke adverse skin reactions.

U.S. Pat. No. 5,669,916 and U.S. Pat. No. 5,989,267 (to Anderson) feature a method involving mechanically or chemically removing of the hair to expose the follicle and then treating topically the follicle by an inactivating compound to inhibit its ability to regenerate a hair. The preliminary removing of the hair facilitates the uptake of the follicle-inactivating compound via the hair duct. The follicle-inactivating compound may be a dye or a photosensitizer, filling the empty follicle, which is submitted thereafter to a light exposure with sufficient energy and for sufficient duration to destroy the follicle. U.S. Pat. No. 5,669,916 discloses the use of 5-aminolevulinic acid (ALA), a photosensitizer precursor of protoporphyrin IX (PpIX), a naturally occurring photosensitizer, which is the immediate precursor of Heme in the Heme bio-synthetic pathway and which may be synthesized in relatively large quantities by certain cells in the presence of ALA. When ALA is administered, the exposition to a light is delayed by several hours for allowing synthesis of PpIX. A drawback of this method is that in a given area of skin all hair follicles are not in same physiological state, that is to say, do not bear a hair at the same time, and thereby cannot be depilated simultaneously. Thus, the Anderson method, unless repeated several times, leads only to the inactivation of a fraction of the follicles present in the treated area.

DE 198 32 221 discloses a similar method of cosmetic hair removal. An ALA based formulation is applied during 15 to 25 hours to a skin area. Thereafter, the treated area is submitted to an irradiation by means of pulsed red light. The hair removal appears effective, if the treatment is repeated about 4 to 8 times, but sunburn like side effects lasting 2 to 20 days after an irradiation are observed.

WO 00/71089 discloses a method for reducing wool growth at the breech or pizzle area of sheep in order to prevent blow-fly strike. The area is treated with an ALA formulation and submitted, optimally, about 8 to 10 hours later, to a light irradiation, including wavelengths 600 to 700 nm. Wool growth is significantly reduced, but treated skin areas of test animals exhibited side effects like edema, discoloration and crusting.

It is on the other hand known that cutaneous administration of ALA results in a localization of ALA predominantly in the superficial skin layers, with a relatively low selectivity versus cell types, and thereby induces a similarly wide spread synthesis of PpIX, so that a subsequent irradiation with visible light results in a non selective damage of various epidermal cell types and tissues, inducing skin damages from transient irritation up to necrosis.

Accordingly, there exists a need for a method for removing hair, that is cheap, that is not time-consuming, painful, and results in hair removal which is long lasting and more permanent than known hair removal methods.

There further exists a need for a method for selectively removing hair without damaging to the skin tissues, in particular without causing irritation, erythema, necrosis or eczema like side effects in the epidermis.

The inventors considered various ways improving the afore-mentioned hair removal method based on administration of a precursor of PpIX and subsequent light irradiation of the skin area to be treated, pertaining to the choice of the photosensitizer precursor, to the technique of administration, and/or to the formulation comprising the administered photosensitizer precursor, for increasing selectivity:

minimizing uptake of the photosensitizer precursor in the epidermis;
minimizing biosynthesis of PpIX in the epidermis;
maximizing catabolism of PpIX in the epidermis;
minimizing phototoxic effect of light exposure in the epidermis;
maximizing selective uptake of the photosensitizer precursor by the pilo-sebaceous apparatus;
maximizing biosynthesis of PpIX in the pilo-sebaceous apparatus;
slowing down catabolism of PpIX in the pilo-sebaceous apparatus;
enhancing phototoxic effect of light exposure in the pilo-sebaceous apparatus.

Whereas previous attempts for maximizing the accumulation of PpIX in the pilo-sebaceous apparatus and enhancing there the effect of light exposure encountered little or poor success, the inventors have now found that improvement of selectivity of the afore-said hair removal method may be achieved by a method minimizing the PpIX level in the epidermis, while obtaining nevertheless an efficient level of PpIX in the pilo-sebaceous apparatus, both simultaneously at the moment of the light irradiation.

According to a first embodiment of the invention, the hair removal method makes use of a compound of formula (I)

$$R^2R^3N-CH_2COCH_2-CH_2COOR \qquad (I)$$

wherein R is $R_n$-$R_1$, wherein $R_n$ represents a polyalkylene glycol chain of formula (II)

$$-[R_{pi}-O]_n- \qquad (II)$$

wherein pi represents n integers, the pi's being equal or different ones from the others, $R_{pi}$ is an alkyl of pi carbon atoms, and n is an integer from 1 to 50, and wherein $R^1$, $R^2$, $R^3$ each separately represent H, or an unsubstituted alkyl, or a substituted alkyl, wherein substituents are selected from aryl, acyl, halo, hydroxy, amino, aminoalkyl, alkoxy, acylamino, thioamino, acyloxy, aryloxy, aryloxyalkyl, mercapto, thio, azo, or oxo, or fluoroalkyl groups, saturated and non-saturated cyclohydrocarbons, and heterocycles, or represent an alkyl chain interrupted by one or more oxygen, nitrogen, sulfur or phosphor atoms, or an alkoxycarbonyloxy, alkoxycarbonylalkyl or methine group, in a method for hair removal from an area of skin of a mammal.

In particular, R may represent a polyalkylene glycol chain of formula (IIa) or formula (IIb)

 (IIa)

 (IIb)

wherein x and y are O or integers, wherein n and x+y are an integer from 1 to 50, wherein Ra and Rb represent independently alkyls from C1 to C4.

In particular, R may represent a short polyethyleneglycol chain of formula (IIc)

 (IIc)

wherein n is an integer from 1 to 5 and R' is a lower alkyl from C1 to C3.

Preferably, in the compound of formula (I), $R^2$ and $R^3$ both represent H, and the compound of formula (I) is in form of an ALA-ester or a pharmaceutically acceptable salt thereof. Most preferably, said compound of formula (I) is ALA-diethylene glycol monoethyl ether ester.

The inventors have found that the substitution of the H of the carboxyl group of ALA by a group of formula (II), or (IIa), or (IIb), or a short chain ester of the polyethylene glycol family, such as formula (IIc), and possibly the substitution of an H of the amino group of ALA by a more lipophilic substituent group, which may also be a group of formula (II), or (IIa), or (IIb) or (IIc), is capable to provide simultaneously, at an appropriate time interval between drug administration and light irradiation, an efficient accumulation of PpIX in the pilo-sebaceous apparatus, comparable to or higher than those obtained by the application of ALA itself, but at the same time, an unexpectedly low PpIX level in the epidermis. Thereby, a light irradiation at that time provides an efficient phototoxic effect in the pilo-sebaceous apparatus, but substantially no damage, or very little damage, to the superficial skin layers.

According to a second embodiment, the inventive method for removing hair from an area of skin of a mammal comprises administration to said mammal of a composition comprising a compound of formula (III),

 (III)

wherein $R^1$, $R^2$, $R^3$ each separately represent H, an unsubstituted alkyl, or a substituted alkyl, wherein substituents are selected from aryl, acyl, halo, hydroxy, amino, aminoalkyl, alkoxy, acylamino, thioamino, acyloxy, aryloxy, aryloxyalkyl, mercapto, thio, azo, or oxo, or fluoroalkyl groups, saturated and non-saturated cyclohydrocarbons, and heterocycles, or represent an alkyl chain interrupted by oxygen, nitrogen, sulfur or phosphor atoms, or an alkoxycarbonyloxy or methine group, and a subsequent light irradiation of said skin area, and further comprises administration to said mammal of an additional agent reducing the PpIX level in the epidermis.

According to a preferred embodiment, said agent comprises at least one compound enhancing the in vivo transformation of PpIX to heme in the epidermis. Metal ions, in particular iron ions, may be supplied as physiologically compatible salts or complexes thereof in a suitable concentration for reducing average PpIx level in epithelium. These compounds act, among others, as co-enzymes and biocatalysts or as regulators of water equivalence and osmotic pressure. Beyond their essential role in tissue growth in humans, metal ions such as, in particular, iron ions are mandatory in the ferrochelatase-mediated transformation of phototoxic PpIX into phototoxically inactive heme. Therefore, the co-administration of bioavailable ferrochelatase, combined or not combined with metal salts, in particular iron salts, with the photosensitizer precursor may decrease unwanted PpIX accumulation in skin layers which should not be damaged, such as the epithelium, while suitable PpIX generation in the pilo-sebaceous apparatus is maintained.

According to a particularly preferred embodiment, said compound comprises and provides iron as Fe (II) to epidermal cells. Fe (II) ascorbate is such a pharmaceutically acceptable iron providing compound. Other examples for such salts include, but are not limited to, oxides, chlorides, sulfates, phosphates, citrates, lactates, glycerophosphates, gluconates, edetates, tartrates, malates, mandelates, benzoates, salicylates, phytates, cinnamates, fumarates, polysaccharide complexes, or amino acid salts. Principally every salt of those elements is suitable for releasing metal atoms, in particular iron, in defined amounts in the skin care compositions according to the invention.

Alternatively, metal ions, in particular iron ions, can be provided in the form of complexes or chelates. Known water-soluble chelates of iron which are relatively or substantially non-toxic are desferrioxamine methanesulfonate, ethylenediaminetetraacetic acid (EDTA) and salts thereof, diethylenetriamine pentaacetic acid (DTPA) and salts thereof, nitrilotriacetic acid (NTA) and salts thereof, trans-1,2-diaminocyclohexane-N,N,N',N'-tetraacetic acid and salts or hydrates thereof, 1,3-diamino-2-hydroxypropyl-N,N,N',N'-tetraacetic acid and salts or hydrates thereof and ethyleneglycol-bis(beta-aminoethyl ether)-N,N-tetraacetic acid, saccharose octasulfate complexes, or 8-hydroxyquinoline complexes.

Metal ions, in particular iron ions, can also be administered under the form of metal-complex binding proteins such as heptoglobin and hemopexin. Furthermore, the cellular uptake of metal ions, in particular iron ions, can be enhanced when uptake-modulating substances such as lactoferrin, transferrin or protein analogous thereof are given alone or along with the metal salts and complexes mentioned above.

The compound enhancing the in vivo transformation of PpIX to heme, in particular the iron providing compound, may be administered before, simultaneously to, or after the administration of the afore-said compound of formula (III). It has been found that is it particularly advantageous to administer said compound enhancing the transformation of PpIX into heme topically to said area of skin, and later than the said compound of formula (III), within the time interval between the drug administration, namely the administration of compound of formula (III), and the light irradiation.

Whereas the administration of a compound enhancing transformation of PpIX to heme may be used in conjunction with the administration of any photosensitizer precursor, it is preferred to use such an agent in conjunction with ALA itself or with ALA-DGME (5-aminolevulinic-diethylene glycol monoethyl ether ester).

Since the bio-synthesis of Heme is temperature dependent, in an embodiment of the method of the invention, the superficial layers of the skin are warmed up from outside, so that bio-synthesis of Heme is accelerated in these superficial epidermal layers but not in the deeper dermal layers.

Whereas the ALA based methods of hair removal of the prior art recommend rather long time intervals between the beginning of drug administration and the beginning of light irradiation of about 8 to 10 hours, or even more than 16 hours, the present inventors have found that side effects, edema, skin irritation and the like may be strongly diminished if the drug/ light interval (DLI) is less than three hours and preferably set between 5 minutes and 2 hours.

Having examined the effects of light dose and light flux on the photo-induced damage of skin portions having received ALA or ALA derivatives, the inventors have found that the photo-induced damage does not depend solely on the total light dose, but depends also on the light flux, the wavelength and the local concentration of sensitizer.

Additionally, it was found that irritation of the superficial skin layers may be diminished if the total light dose necessary to induce the photochemical reactions necessary to damage a pilo-sebaceous apparatus are delivered at a relatively moderate light flux (irradiance) of less than 80 mW/cm$^2$ at wavelengths above 600 nm, preferably around 635 nm.

The method of the invention may employ a specific sequence of light irradiations, comprising at least a first irradiation performed with poorly penetrating wavelengths, that is to say smaller than 600 nm, preferably around 400 nm. The first irradiation is followed by at least a second irradiation performed with light having a more penetrating wavelength, above 600 nm, preferably with red light around 635 nm, and with a sufficient total dose, but at a sufficiently small light flux to damage the pilo-sebaceous apparatus, while sparing the epidermis in which the PpIX has been degraded with the first irradiation. Thus, a selective destruction of PpIX in the epidermis can be first achieved by irradiating the skin with a poorly penetrating wavelength. This irradiation will degrade the PpIX in the epidermis while generating minimal tissue destruction in this tissue layer. The PpIX located in the pilo-sebaceous apparatus will not be significantly excited, due to the poor penetration of the wavelength mentioned above. A subsequent irradiation of the skin with a longer, more penetrating wavelength, and with a sufficiently small light flux damages then the pilo-sebaceous apparatus while sparing the epidermis, in which the PpIX has been degraded with the first irradiation.

According to another embodiment of the method of the invention, the phototoxic effects induced by the irradiation can be selectively reduced in the epidermis by administering topically antioxidants or free radical scavengers, or substances reacting with singlet oxygen. Examples of such substances are vitamin B6, C, ascorbic acid, E (tocopherols) and derivatives thereof (ester), vitamin A and carotenoids (alpha, beta and gamma-carotene, lycopene, lutein, etc.), retinoids, azides, superoxyde-dismutase, butyl-hydroxytoluene, 1,4-diazabicyclo [2,2,2] octane, histidin, L-tryptophan, n-acetyl-1-cysteine, 1-cysteine, s-adenosyl-1-methionine, melatonin, 1-melatonin, DHEA or other hormones with antioxidant activity, glycine, mannitol, reduced or non-reduced glutathione, Se-glutathione peroxidase, Fe-catalase, NADPH, ubiquinol (reduced coenzyme Q10), Zn-superoxide dismutase (SOD), Mn-SOD, Cu-SOD, uric acid, lipoic acid, alpha-hydroxy acids, metal binding proteins including albumin (and albumin bound thriols and bilirubin).

According to another embodiment, agents may also be used to reduce the PpIX synthesis efficacy in the epidermis. Particularly preferred additives are inhibitors of protoporphyrinogen oxidase, a mitochondrial enzyme responsible for the conversion of protoporphyrinogen to PpIX. Surprisingly, whereas publications in the agricultural and biomedical fields report an increase of PpIX production after administration of inhibitors of this enzyme, the inventors found that this additive decreases the overall PpIX production in certain cell cultures (T24 bladder cells); the mechanism is not fully understood.

A composition containing the photosensitizer precursor may also contain one or several agents enhancing penetration ability of the sensitizer precursor down to the hair follicle and sebaceous gland, or increase bio-synthesis of PpIX, or inhibit there further bio-chemical steps leading from PpIX to heme. Preferred agents are DGME, DMSO, EDTA, alcohols, in particular ethanol, and deferoxamine. Deferoxamine is particularly preferred since this substance is not able to cross the stratum corneum but is able to migrate along a hair duct, and thereby increases the difference in PpIX accumulation between follicles and surrounding tissues.

The above-mentioned agents and additives may be formulated together with a compound of formula (I) or (III) for topical administration. Topical compositions include, but are not limited to, solutions, gels, creams, ointments, sprays, lotions, salves, sticks, soaps, powders, pessaries, aerosols, and other conventional pharmaceutical forms in the art, which may be administered with or without occlusion.

Solutions may, for example, be formulated with an aqueous or alcoholic base containing one ore more emulsifying, surfacting, dispersing, suspending, penetration enhancing, or thickening agent.

Ointments and creams may, for example, be formulated with an aqueous or oily base with the addition of suitable thickening and/or gelling and/or surfacing agents.

Lotions may be formulated with an aqueous or oily base and will, in general, also contain one or more emulsifying, surfacting, dispersing, suspending, or thickening agent. Suitable surfacting agents are lauryl derivatives.

The compounds according to the invention may be provided in liposomal formulations. Pharmaceutically acceptable liposomal formulations are well-known to persons skilled in the art and include, but are not limited to, phosphatidyl cholines, such as dimyristoyl phosphatidyl choline (DMPC), phosphatidyl choline (PC), dipalmitoyl phosphatidyl choline (DPPC), and distearoyl phosphatidyl choline (DSP), and phosphatidyl glycerols, including dimyristoyl phosphatidyl glycerol (DMPG) and egg phosphatidyl glycerol (EPG). Such liposomes may optionally include other phospholipids, e.g. phosphatidyl ethanolamine, phosphatic acid, phosphatidyl serine, phosphatidyl inositol, abd disaccarides or poly saccarides, including lactose, trehalose, maltose, maltotriose, palatinose, lactulose, or sucrose in a ratio of about 10-20 to 0.5-6, respectively.

In order to permit sequential delivery of compounds of formula (I) or (III) and of additional agents, taking into account the kinetics of PpIX synthesis in different tissues, in particular for delivering in a first step a photosensitizer precursor according to formula (I) or (III), and for delivering in a second step an agent diminishing the PpIX level in the epidermis, before performing the step of irradiating the concerned area of skin, the formulation including the compound of formula (I) or (III) and the formulation containing the afore-said agents and additives should be provided in separate vials within a same commercial kit.

Synthesis of PpIX in a hair follicle is depending upon the growing state of the hair. For enhancing the efficiency of the method, most hair follicles of a treated skin area should be as far as possible in the same growing phase. The method according to the invention may thus be preceded by a preliminary synchronization step, by means of substances like minoxidil and/or by a preliminary epilation. A synchronizing agent like aminoxidial-based formulation may be provided in the afore-mentioned kit.

The inventors found that a preliminary removal of the greasy and/or lipophylic substances from surface of the skin, for example by means of acetone or alcoholic solutions, enhances build up of PpIX in the pilo-sebaceous apparatus. Such degreasing agents may be included in the afore-said kit.

Advantages of the invention will further appear to those skilled in the art by the following description of results evidencing increased selectivity by means of a preferred photo-sensitizer precursor,
of a preferred iron providing agent and
of preferred operative conditions,
in relation to the figures, wherein:

FIGS. 1, 2, 3, 4 and 5 are fluorescence images of human forearm or leg skin areas of 2.5 cm in diameter, the pictures being taken three hours after administration of photosensitizer precursors under variable experimental conditions described in details hereunder;

Figures 6A, 6B:
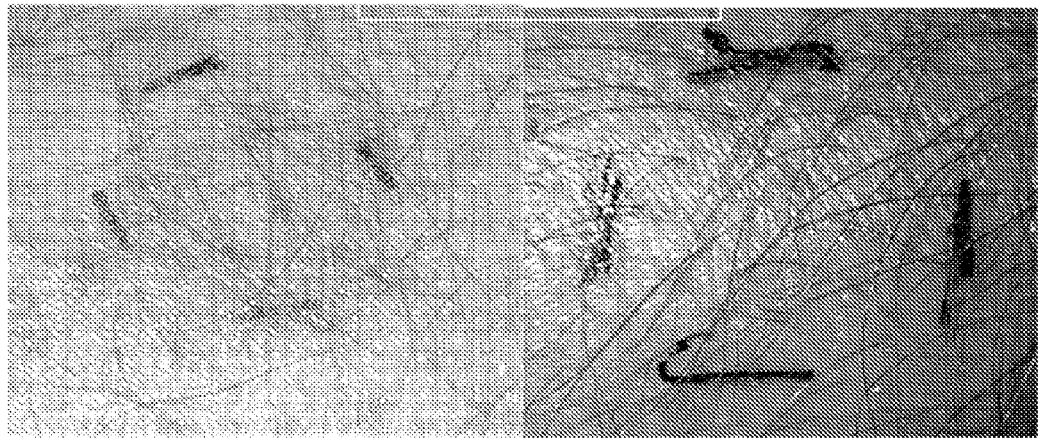
FIGS. 6, 7 and 8 are photos of skin areas taken after the irradiation step, under various conditions described in details hereunder.

In all assays, ALA was used as the commercially available 5-amino-levulinic acid hydrochloride without further purification.

h-ALA, the n-exyl ester of ALA, was prepared according to the synthesis described in WO 96/28412.

ALA-DGME, diethylene glycol monoethyl ether 5-aminolevulinate was synthesized as follows:

Reagents were used as acquired from commercial sources without purification. Anhydrous solvents were obtained by distillation over an adequate drying agent. Solvent was removed by rotary evaporation under reduced pressure, and silica gel chromatography was performed using Merck silica gel 60 with a particle size of 40-63 µm. The purified compounds were analyzed by thin-layer chromatography (silica gel 60 F254 0.2 mm, Merck, solvent $CH_2$—$Cl_2$/$CH_3OH$ 95:5, detection with KMnO4) and $^1$H-NMR on a Bruker AMX 400.

0.5 ml of thionyl chloride were added drop by drop under stirring to an excess (~6 ml) of Diethylene glycol monoethyl ether cooled on ice in an argon atmosphere. The solution was stirred for a further 60 minutes to bring the reaction to completion; after warming up to room temperature, 1 g of ALA (Mr=167.6 g/mol) was added to the solution. The suspension was then stirred over night at 40° C. under argon. The final phase of the reaction was controlled on-line by thin layer chromatography (TLC) (TLC foils, Schleicher & Schuell, Merck, Darmstadt, Germany) in $CH_2Cl_2$/MeOH (95:5) stained by KMnO4 (Rf=0.65). Once the reaction was complete, the solvent was removed under reduced pressure (~0.5 torr) and residuals were applied to a silica chromatography column (silica gel (Merck), eluent: dichloromethane/methanol 95/5) to provide the product as a yellowish liquid of oily appearance.

Compound ALA-DGME: 87% yield; mp 25.0-30.0° C.; $^1$H NMR (400 MHz, $D_2O$) δ 4.20-4.18 (m, 2H, $H_2C(1^2)$), 4.05 (s, 2H, $H_2C(5)$), 3.70-3.68 (m, 2H, $H_2C(1^3)$), 3.63-3.61, 3.59-3.56 (m, 2H, m, 2H, $H_2C(1^4)$, $H_2C(1^5)$), 3.51 (q, $^3J(1,^6\ 1^7)$ 7.1, 2H, $H_2C(1^6)$), 2.87-2.83 (m, AA' of AA'BB'-system, 2H, $H_2C(3)$), 2.68-2.65 (m, BB' of AA'BB'-system, 2H, $H_2C(2)$), 1.11 (t, $^3J(1,^6\ 1^7)$ 7.1, 3H, $H_3C(1^7)$).

The photosensitizer precursors were formulated within standard excipients of the European Pharmacopoeia, namely unguentum leniens (UL) and unguentum hydrophilicum anionicum (UH); for some essays, the photosensitizer precursors were suspended either in pure glycerol (GLY) or in pure diethylene glycol monoethyl ether (DGME).

The formulations were administered topically on the forearm or the leg using the Tegaderm™ transparent dressing. This dressing enables the transport of water and oxygen according to the specifications of the manufacturer. This dressing was removed and the remaining formulation cleaned with pure ethanol just before the measurements performed at one single point in time. For the pharmacokinetic measurements, this dressing was removed after four hours. This removal of the Tegaderm™ during the remaining time course of the measurements induced negligible minimal alterations of the measurements due to the excellent transparency of this dressing at the wavelengths of interest.

Figure 9:
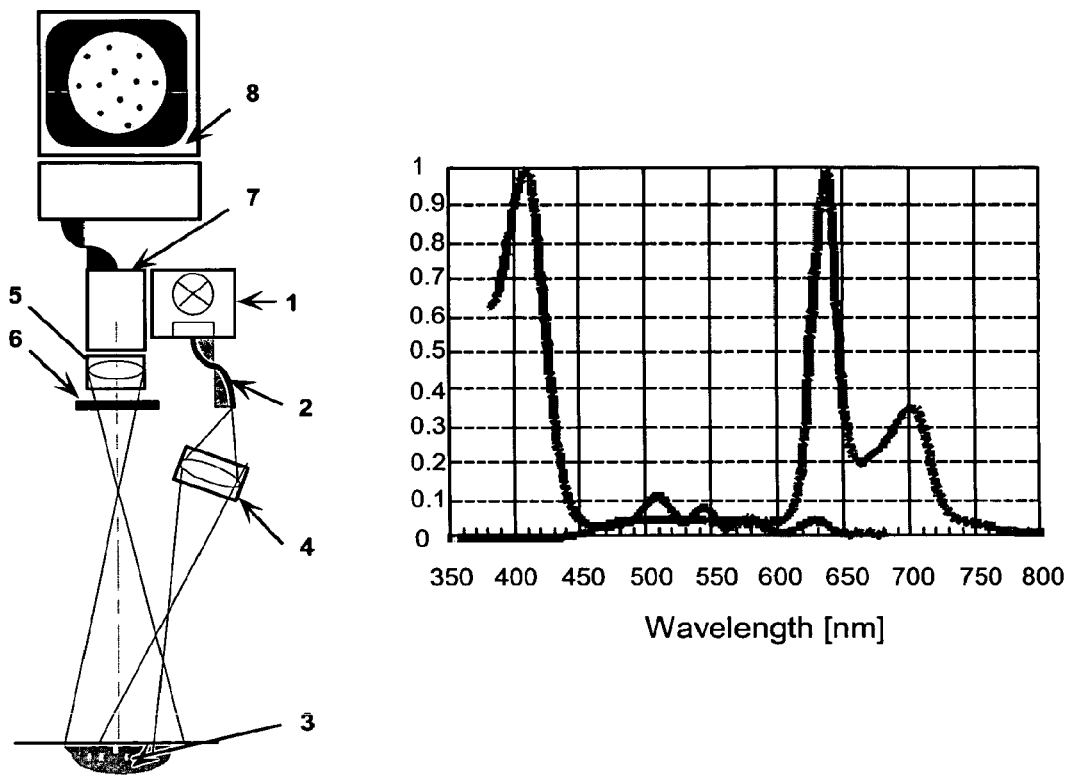
FIG. 9 is a schematic view of the instrumentation for macroscopic fluorescence imaging.

A fluorescence imaging system illustrated by FIG. 9 was developed to assess the extent and level of PpIX production in "macroscopic" samples (parts of the human body such as: forearm, leg, back, etc.). As the goal is to assess the relative level of PpIX in the hair follicle of these samples, red light at 635 nm was chosen as PpIX fluorescence excitation wavelength. It is indeed well known that red light penetrates deeper in the cutaneous tissues than green and violet light, the later two wavelengths corresponding to larger PpIX absorption peaks (see the PpIX fluorescence excitation and emission spectra presented on the right side in FIG. 9).

As presented in the schematic diagram presented in FIG. 9, this fluorescence imaging system involves a modified 300 W D-light source 1 (Xe arc lamp from Storz, Tuttlingen, Germany) equipped with a red bandpass filter (635 nm, 20 nm FWHM; Chroma, USA). This fluorescence excitation light is coupled in a Storz 4 mm diameter light guide 2. The output of this light guide is imaged on the tissue sample 3 with a projection objective 4 (Nikon, Japan; AF Nikkor; 1:1.4 D/50 mm) to generate a homogenous spot of 2.5 cm in diameter with an irradiance of 2 mW/cm$^2$ at 635 nm. The distance between this projection objective 4 and the sample 3 is 25 cm. Therefore, the light beam illuminating the sample can be considered as parallel. The fluorescence is collected by another objective 5 (Fujinon, Japan; TV zoom lens; 1:1.2/ 12.5-75 mm; Type H6X12.5R-MD3) through a longpass filter 6 (Schott, Germany; RG665) and the image detected by a scientific CCD camera (752×582 pixels CF 8/1 Kappa, Gleichen, Germany) equipped 7 with an image intensifier (Proxifier BV 256-2FcZ-CH, Proxitronic, Bensheim, Germany). The images are captured by the 8-bits camera frame grabber and saved on the computer 8 with the "Kappa Imagebase-control" software. Image treatment is carried out using the IPLab imaging software. The spatial resolution of the complete setup has been measured with an USAF resolution target and the value we obtained in the sample plan is 3 lp/mm, the size of the image detected by the camera being 3×4 cm$^2$. A reference sample has been designed to enable a comparison of the relative fluorescence brightness between samples investigated at different times. This reference consists of a ruby disk (diameter: 12 mm; thickness: 1.02 mm; Type 8Sp3, Hans Stettler SA, Lyss, Switzerland) covered with a neutral density filter (T=2.27%) so that the signal obtained with this reference sample corresponds to the typical tissue fluorescence detected in our conditions.

The images were analyzed using the NIH image software. The method consisted in identifying the location of an area corresponding to: 1) one typical hair follicle and 2) epidermis presenting no skin appendages. The number of pixels involved in such an area was typically 100. The value of these pixels was averaged, corrected by subtracting the tissue autofluorescence recorded at a location which did not received any PpIX precursor and normalized with the value of the ruby reference mentioned above. Thus, for each tested formulation, areas surrounding a hair follicle receive a fluorescence brightness value and areas of the epidermis bearing no hair also receive a fluorescence brightness value, these values being expressed in arbitrary relative units, relative to the reference being the above-mentioned ruby disk. The ratio r=fluorescence brightness value of a hair follicle area/fluorescence brightness value of a hairless epidermis area is used to quantify the selectivity of the method in order to compare various operating conditions as set forth below:

FIGS. 1A and 1B illustrate the improvement of follicle/epidermis selectivity by the addition of iron ascorbate:

FIG. 1A shows a fluorescence image taken three hours after administration of a composition containing 20% ALA in unguentum hydrophilicum without iron; ratio r=1.46;

FIG. 1B shows such a skin area three hours after administration of a composition containing 20% ALA and 3% of iron ascorbate in unguentum hydrophilicum; ration r=2.53.

FIG. 1B shows fluorescence brightness more localized around the hair follicles than in FIG. 1A, thereby demonstrating an improved selectivity by means of addition of the iron salt.

FIGS. 2A, 2B and 2C demonstrate the improvement of follicle/epidermis selectivity by non-simultaneous administration of PpIX precursor and iron ascorbate:

FIG. 2A is a picture taken in following conditions administration of iron ascorbate 5% in Essex™ creme (Essex Chemie AG, Switzerland); after one hour, removal of this creme by wiping with ethanol; then, administration of ALA-DGME 95% with 5% iron ascorbate during three hours; ratio r=1.93;

FIG. 2B: Administration of ALA-DGME 95% together with 5% iron ascorbate during three hours; ratio r=5.95;

FIG. 2C: Administration of ALA-DGME 100% during two hours; then removal of this formulation by wiping with ethanol and administration of ALA-DGME 95% with 5% iron ascorbate during one hour; ratio r=7.15.

The administration protocol pertaining to FIG. 2A results in poor selectivity; the administration protocol pertaining to FIG. 2B results in an improved selectivity, but the best selectivity is obtained by the administration protocol pertaining to FIG. 2C. Without being bound by theory, it seems that the kinetics of Fe (II) ascorbate uptake and the reactions PpIX→heme are faster than the kinetics of the reactions ALA→PpIX. Therefore, the photosensitizer precursor should be administered during an appropriate time to build up PpIX levels in the pilo-sebaceous apparatus and, thereafter, the iron compound should be administered onto the skin for a relatively short time interval for decreasing the PpIX level in the epidermis before the irradiation step.

FIGS. 3 and 4 show that the sensitizer precursor ALA-DGME provides a substantive improvement of follicle/epidermis selectivity as compared to the use of ALA itself:

FIG. 3A is an image taken after three hours administration of ALA 20% in glycerol; ratio r=1.62;

FIG. 3B is an image taken after three hours administration of ALA-DGME 20% in glycerol; ratio r=2.51;

FIG. 4A is an image taken after three hours administration of ALA 20% in DGME; ratio r=2.21;

FIG. 4B is an image taken after three hours administration of ALA-DGME 20% in DGME; ratio r=3.24.

FIGS. 3B and 4B both show improved selectivity of ALA-DGME versus ALA, namely built up of PpIX fluorescence in the pilo-sebaceous apparatus, and very low fluorescence in the epidermis.

Comparison of widths of fluorescence spots in FIGS. 2B and 4B suggest that the generation of PpIX may occur at variable depth in the pilo-sebaceous apparatus, depending upon the compound used as photosensitizer precursor. Therefore, it may be useful to co-administer more than one compound to generate phototoxic effects simultaneously at different depths.

FIGS. 5A and 5B show the influence of temperature on the PpIX build up: pure ALA-DGME was applied onto two spots, one on each lower leg of the same patient, and covered by the aforementioned Tegaderms™ dressings. One site was then covered with an electric blanket (Solis AG, Fusswaermer, Switzerland) and hold at a temperature of 41° C. The temperature was controlled by a thermo couple inserted below the blanket in direct contact with the skin. The site on the opposite lower leg was covered by the Tegaderm™ dressing only: this is why the skin temperature was around 31° C. in this case. The Tegaderm™ dressings and the electric blanket were removed after 3 hours and the PpIX fluorescence imaged and measured immediately after.

FIG. 5A shows the skin maintained at normal skin temperature of 31° C.; the ratio r is 3.47. FIG. 5B shows the skin maintained during three hours at 41° C.; the ratio r is 4.72. In the latter case, one observes a higher selectivity. Without being bound by theory, it may be assumed that the conversion of PpIX to heme was accelerated in the epidermis in the latter case, whereas the heating blanket had no or little effect on the deeper tissues.

The irradiation step of the skin areas treated by means of the various photosensitizer precursor compositions described above was conducted as follows: The irradiation of the skin was performed at 635 nm with an argon ion (Spectra-Physics, model 2020) pumped dye laser (Spectra-Physics, model 375B). The light was coupled in a frontal FD1 light distributor from Medlight SA (Ecublens, Switzerland). This distributor generated a uniform 2 cm in diameter spot. The typical irradiances and light doses were 60 to 130 mW/cm$^2$ and 30 to 130 J/cm$^2$, respectively. The irradiance was checked before and after all treatments. The light power delivered by the light distributor was determined using a power meter from Spectra-Physics (Model 407A, Mountain view, Calif., USA).

Figures 8A, 8B:
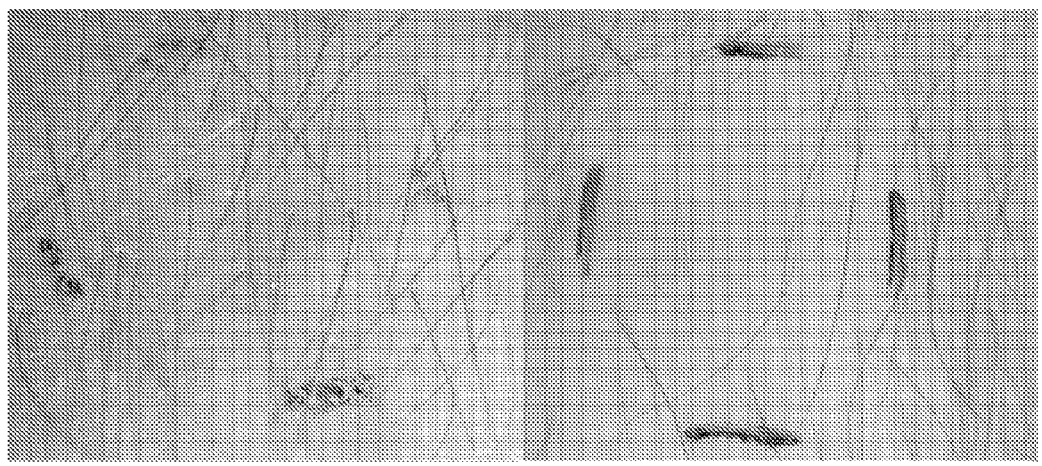

FIGS. 8A and 8B demonstrate the efficiency of a formulation including both ALA and iron ascorbate. A formulation in unguentum hydrophilicum comprising 20 W ALA and 3% iron ascorbate was administered during 195 minutes. Thereafter, the skin was cleaned as indicated above. 15 minutes later, the skin area was irradiated with a light dose of 127 J/cm$^2$ at an irradiance of 127 mW/cm$^2$.

FIG. 8A shows a picture of the skin area after one day: all hairs are still present;

FIG. 8B shows a picture of the same area eight days later: most hairs have disappeared, demonstrating the efficiency of ALA iron formulations.

FIGS. 6A and 6B show that upon use of formulations including ALA and iron ascorbate, setting the drug/light time interval to short times diminishes the side effects in the epidermis. A formulation containing 20% ALA and 3% of iron ascorbate in unguentum hydrophilicum was applied during three hours to the skin of a leg. A first area was submitted to light irradiation after a waiting time equal to 200 minutes with a light dose of 61 J/cm$^2$ at an irradiance of 42.4 mW/cm$^2$. This area, as shown by the FIG. 6A taken one day after the irradiation, developed redness/irritation. A second area was submitted to light irradiation 30 minutes after the end of drug administration. The light dose was 130 J/cm$^2$ at an irradiance of 56.6 mW/cm$^2$. As shown in FIG. 6B, this skin area did not exhibit any adversely irritated aspect one day after irradiation.

Figure 7:
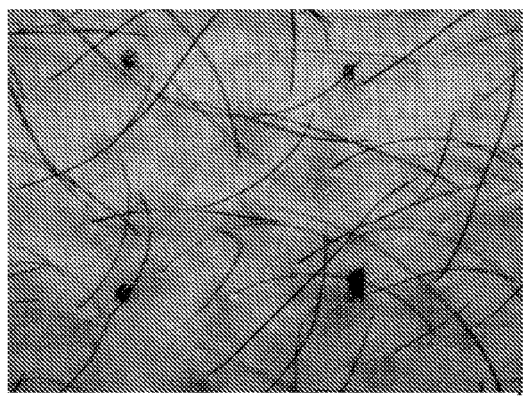

FIG. 7A shows a skin area on which pure ALA-DGME was applied during 195 minutes. Thereafter, the skin was cleaned and irradiated 200 minutes later with a light dose of 30 J/cm$^2$ at an irradiance of 65 mW/cm$^2$. The picture shown by FIG. 7A was taken one day after irradiation and shows a clear reaction selectivity between the skin areas around follicles and the epidermis in bulk.

Figure 10:
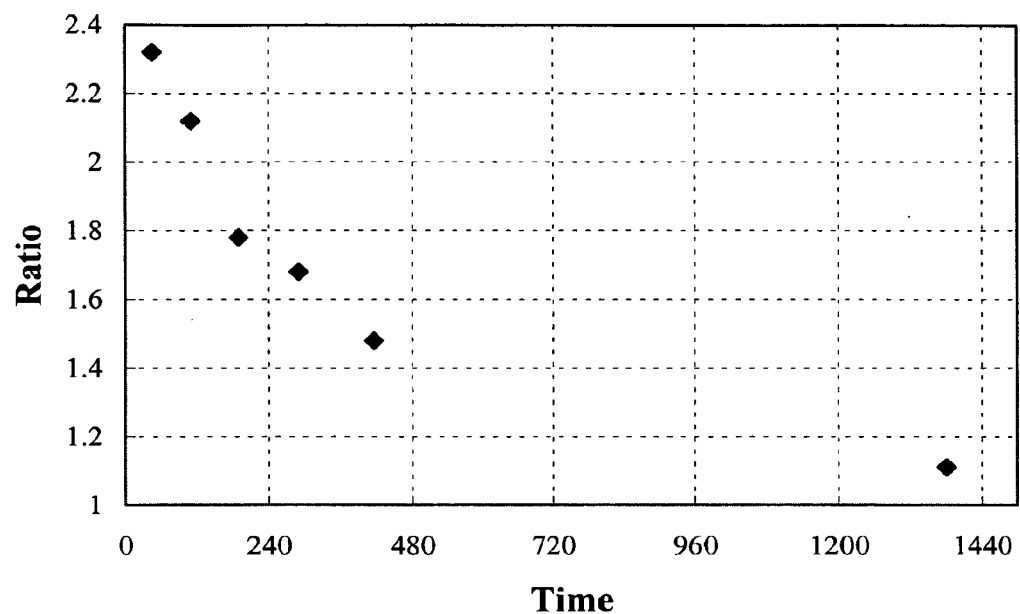
FIG. 10 is a diagram showing the kinetics of the ratio hair follicle/epidermis fluorescence.

FIG. 10 presents an example of kinetics of the hair follicle/epidermis fluorescence ratio, namely the results obtained after administration of methyl ester of ALA (m-ALA) to one male volunteer. The precursor concentration was 20% in Unguentum Leniens (Merck, Darmstadt, Germany). The superficial PpIX fluorescence was measured for the spots corresponding to the hair follicle and the epidermis from 0 to 1380 minutes. The data presented in this figure are the ratio between these two values, versus time. It should be noted that all the PpIX fluorescence intensities from which the ratios were deduced were expressed in relative units. This means that they are not absolute physical values but can be compared at different times for the same type of tissue (hair follicle or epidermis). This limitation is due to the spatial origin of the PpIX fluorescence, which comes from very different depths between the epidermis and the hair follicle. The absolute value of the hair follicle/epidermis fluorescence ratio is therefore meaningless, but its value can reasonably be considered as proportional to the true PpIX concentration ratio for different times after administration.

It can be seen from FIG. 10 that the hair follicle/epidermis ratio decreases rapidly during the first hours and tends to unity for longer times. This observation suggests that the irradiation will have to be performed during the first hours after the beginning of the formulation administration to take profit of this intrinsic selectivity.

The invention claimed is:

1. A method of removing hair from an area of skin of a mammal, comprising:
    administering topically to a skin area a composition comprising a compound of formula:

wherein R is a polyethylene glycol chain of formula:

wherein n is an integer from 1 to 5 and R' is a lower alkyl from C1 to C3, and wherein $R^2$ and $R^3$ each separately represent H, or an unsubstituted alkyl, or a substituted alkyl, wherein substituents are selected from aryl, acyl, halo, hydroxy, amino, aminoalkyl, alkoxy, acylamino, thioamino, acyloxy, aryloxy, aryloxyalkyl, mercapto, thio, azo, oxo or fluoroalkyl groups, saturated and non-saturated cyclohydrocarbons, and heterocycles, or represent an alkyl chain interrupted by oxygen, nitrogen, sulfur or phosphor atoms, or an alkoxycarbonyloxy, alkoxycarbonylalkyl or methane group, and
    irradiating said skin area with optical energy having a light flux of less than 80 mW/cm² and a wavelength above 600 nm after administration of said composition, wherein said skin area is submitted to said irradiation within a time interval of between from 5 minutes to 10 hours starting from the beginning of the administrating of said composition.

2. The method according to claim 1, comprising administering a composition of a compound of formula (I), wherein $R^2$ and $R^3$ both represent H and said compound is in form of an ALA-ester or a pharmaceutically acceptable salt thereof.

3. The method according to claim 2, wherein said compound of formula (I) is ALA-diethylene glycol monoethyl ether ester or a pharmaceutically acceptable salt thereof.

4. The method as claimed in claim 3, wherein ALA-DGME is administered in substantially pure, non solid form.

5. The method as claimed in claim 1, wherein said time period is less than 3 hours.

6. The method according to claim 1, further comprising providing selective accumulation of PpIX in the pilo-sebaceous apparatus of the epidermis of a mammal by administering a composition of a compound of formula (I).

7. The method as claimed in claim 1, further comprising administering an agent reducing the level of PpIX in the epidermis to said mammal.

8. The meth as claimed in claim 7, wherein said agent comprises at least one compound enhancing the in vivo transformation of PpIX to heme in the epidermis in said skin area.

9. The method as claimed in claim89, wherein said compound is an iron providing compound.

10. The method as claimed in claim 9, wherein said compound is Fe(II) ascorbate.

11. The method as claimed in claim 8, wherein said compound enhancing the transformation of PpIX into heme is administered topically to said skin area later than said compound of formula (I), within the time interval between the beginning of administration of said compound of formula (I) and said light irradiation.

12. The method as claimed in claim 11, wherein said time interval is of between 5 minutes to 3 hours.

13. The method as claimed in claim 7, wherein said agent is a protoporphyrinogen oxidase inhibitor.

14. The method as claimed in claim 1, wherein said composition further comprises at least one topically administered agent selected from the group consisting of antioxidants, free radical scavengers and substances reacting with singlet oxygen.

15. The method as claimed in claim 1, wherein said composition further comprises an agent selected from agents enhancing penetration ability of said compound of formula (I) in the pilo-sebaceous apparatus.

16. The method according to claim 1, comprising irradiating said skin area at least with a first optical energy having a wavelength below 600 nm, and at least with a second optical energy having wavelength above 600 nm with a light flux below 80 mW/cm².

17. The method according to claim 1, and further comprising applying warming means to said skin area during the administration of said composition.

18. The method according to claim 1, comprising co-administration of two compounds of formula (I).

* * * * *

UNITED STATES PATENT AND TRADEMARK OFFICE
CERTIFICATE OF CORRECTION

PATENT NO. : 8,235,974 B2
APPLICATION NO. : 10/495803
DATED : August 7, 2012
INVENTOR(S) : Georges Wagnieres et al.

It is certified that error appears in the above-identified patent and that said Letters Patent is hereby corrected as shown below:

At column 11, lines 33-34, please delete the phrase:

"administering topically to a skin area a composition comprising a compound of formula:"

and insert the phrase:

--administering topically to a skin area a composition comprising a compound of formula (I):--

At column 11, line 37, please delete the phrase:

"wherein R is a polyethylene glycol chain of formula:"

and insert the phrase:

--wherein R is a polyethylene glycol chain of formula (IIc):--

At column 11, line 38, please delete the formula "((CH2)2-O)nR'"

and replace with

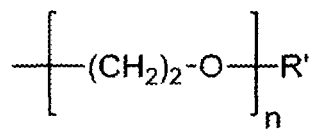

At column 12, line 19, please delete the term "meth" and insert the term --method--.

At column 12, line 22, please delete "claim89" and insert the phrase --claim 8--.

Signed and Sealed this
Fifth Day of March, 2013

Teresa Stanek Rea
*Acting Director of the United States Patent and Trademark Office*